United States Patent
Holmén

(10) Patent No.: US 6,533,769 B2
(45) Date of Patent: Mar. 18, 2003

(54) METHOD FOR USE IN CATARACT SURGERY

(76) Inventor: Jörgen Holmén, Kulla, Bällefors, S-549 93 Moholm (SE)

(*) Notice: Subject to any disclaimer, the term of this patent is extended or adjusted under 35 U.S.C. 154(b) by 0 days.

(21) Appl. No.: 09/848,784

(22) Filed: May 3, 2001

(65) Prior Publication Data

US 2002/0165522 A1 Nov. 7, 2002

(51) Int. Cl.[7] .................................................. A61M 31/00
(52) U.S. Cl. ........................ 604/521; 128/898; 623/6.56
(58) Field of Search .................. 604/506, 521; 128/898; 623/4.1, 6.11, 6.56; 435/183; 514/2

(56) References Cited

U.S. PATENT DOCUMENTS

| | | | | |
|---|---|---|---|---|
| 4,909,784 A | | 3/1990 | Dubroff ........................ 604/49 |
| 5,013,295 A | | 5/1991 | Dubroff ........................ 604/38 |
| 5,188,590 A | * | 2/1993 | Dubroff ........................ 604/22 |
| 5,204,331 A | | 4/1993 | Nishi et al. .................... 514/54 |
| 5,375,611 A | * | 12/1994 | Lindqvist et al. ............. 128/898 |
| 5,445,636 A | * | 8/1995 | Bretton ........................ 604/22 |
| 5,616,122 A | * | 4/1997 | Lam et al. ................... 514/912 |
| 5,620,013 A | * | 4/1997 | Bretton ........................ 128/898 |
| 5,696,091 A | * | 12/1997 | York et al. .................... 424/427 |
| 5,760,075 A | * | 6/1998 | Stjernschantz et al. ...... 514/530 |
| 5,779,472 A | * | 7/1998 | Meyer ............................ 433/91 |
| 5,792,099 A | * | 8/1998 | DeCamp et al. ............. 604/117 |
| 5,885,279 A | * | 3/1999 | Bretton ........................ 606/41 |
| 5,972,889 A | * | 10/1999 | Courtois ...................... 424/422 |
| 6,027,531 A | * | 2/2000 | Tassignon ................... 128/898 |
| 6,074,358 A | * | 6/2000 | Andrew et al. ............. 604/113 |
| 6,089,234 A | * | 7/2000 | Bretton ........................ 128/898 |
| 6,186,148 B1 | * | 2/2001 | Okada ......................... 128/898 |
| 6,254,587 B1 | * | 7/2001 | Christ et al. .................. 604/22 |
| 6,261,321 B1 | * | 7/2001 | Kellan ........................ 623/6.43 |
| 6,319,222 B1 | * | 11/2001 | Andrew et al. ............. 604/113 |
| 6,367,480 B1 | * | 4/2002 | Coroneo ..................... 128/898 |

* cited by examiner

*Primary Examiner*—Michael J. Hayes
*Assistant Examiner*—Mark Han
(74) *Attorney, Agent, or Firm*—Jenkens & Gilchrist, P.C.

(57) ABSTRACT

A method for treatment of residual lens epithelial cells is disclosed. The method provides increased safety during local treatment in ocular surgery by improved administration of active agents. The method is particularly useful in treatment of proliferative events in ocular surgery, such as posterior capsular opacification.

28 Claims, 7 Drawing Sheets

METHOD FOR USE IN CATARACT SURGERY

TECHNICAL FIELD OF THE INVENTION

The present invention relates to cataract surgery, specifically to a method for preventing proliferation of remaining lens epithelial cells after cataract surgery.

BACKGROUND OF THE INVENTION

The crystalline lens of the human eye is located in the posterior chamber between the posterior iris surface and the vitreous body. It is a biconvex transparent tissue without nerves and blood vessels, weighing approximately 0.2 g. The lens is enveloped in a capsule, a structureless, transparent and elastic membrane bag. Approximately 80 zonular fibres, extending between the capsule and the ciliary body, suspend the lens. The inside of the lens capsule consists of lens epithelial cells and lens fibres. The lens epithelial cells form a monolayer underlying the capsule from the anterior pole to the equator of the lens. These cells continue to undergo cell mitosis throughout life in the area located between the anterior pole and the lens equator. The lens epithelial cells that underwent cell mitosis gradually move toward the lens equator and differentiate into lens fibres. These cells make up the rest of the lens. New layers of fibre cells are constantly formed on top of those previously formed. The older fibre cells become denser and during the $3^{rd}$ decade of life a hard nucleus is formed in the middle of the human lens, consisting of old dehydrated fibre cells.

A cataract is defined as every form of opacity in the lens or its capsule; the lens becomes cloudy, resulting in a loss of visual ability. A cataract is a painless phenomenon, but decreases the quality of life if the lens is not surgically extracted and replaced by an artificial lens.

When the lens is surgically extracted, an incision is made in the anterior part of the eye, i.e., the cornea or the sclera. Then, a viscoelastic material is usually introduced into the anterior chamber to maintain the anterior chamber depth during surgery. An opening is made in the lens capsule by a procedure called capsulorhexis.

Following capsulorhexis, the lens is removed according to one of two principles: extracapsular cataract extraction (ECCE)—the cataractous lens is squeezed out through an opening in the anterior lens capsule and then removed through a 10–12 mm corneal incision, or phacoemulsification—the cataractous lens is dissolved with a special instrument, phaco-probe, by high frequency sonification and rinsed out through a 3–4 mm corneal incision.

Remaining parts of the lens, i.e. lens fibres and lens epithelial cells, are then removed using an irrigation and aspiration device. After complete removal of the lens, the lens capsule is filled with a viscoelastic material and an artificial lens is implanted into it.

Dyeing of the anterior lens capsule has been used to facilitate capsulorhexis in advanced/white cataract, to enhance critical steps during phacoemulsification and to perform capsulorhexis of the posterior lens capsule. Earlier studies have evaluated dyes, such as crystal violet, fluorescein, and indocyanine green, for dyeing the anterior lens capsule. Some dyes are applied by injection under the anterior surface of the capsule. Others are applied by a certain technique in which the anterior chamber is filled by air, and the dye is applied on top of the anterior surface of the capsule. After a while, the dye is washed away by irrigation/aspiration and the anterior chamber is filled by a viscoelastic solution followed by capsulorhexis.

After cataract surgery, the most common postoperative complication is posterior capsule opacification (PCO) which has the clinical and economic significance to be considered as an important public health problem. Studies report that the incidence of PCO is ranging from 20% to 40% after approximately 4 years after surgery. Migration and proliferation of remaining lens epithelial cells is the main cause of PCO. These cells grow from the peripheral parts of the capsule onto the posterior capsule and continue toward the axial region. Impaired visual acuity is the result caused by cell migration, proliferation and aggregation, the production of extracellular matrix, fibrosis and wrinkling of the lens capsule.

In the current clinical standard, patients who develop PCO are treated by YAG laser to capsulotomy. In this procedure a YAG laser disrupts the opacified lens capsule and the visual axis is cleared. However, YAG laser capsulotomy exposes patients to the risk of complications that can lead to severe visual impairment or loss of vision, such as retinal detachment, pupillary block glaucoma and cystoid macular edema. Other complications associated with YAG laser capsulotomy include damage to implanted intraocular lenses resulting in glare and photophobia, dislocation of intraocular lenses, iritis, vitritis, corneal edema, iris damage and rupture of the anterior hyaloid.

From an economic point of view, the treatment of PCO is ranked one of the highest of the medical costs in the U.S.A. Thus, development of a procedure to prevent PCO reduces the medical costs related to YAG laser capsulotomy, including the costs for the treatment, its complications, and YAG laser equipment. Accordingly, there is a great need for a way to prevent PCO.

Mechanical and pharmaceutical methods to prevent PCO by removing or destroying residual lens epithelial cells have been developed. However, none of them has been proved to be practical, effective, and safe enough for routine clinical practice.

Capsular polishing, aspiration of residual lens epithelial cells, ultrasound combined with aspiration, cryocoagulation, and osmolysis are examples of methods that have been developed and shown to remove or destroy remaining lens epithelial cells, but none of these methods have been proven to prevent PCO effectively.

The design of the artificial intraocular lenses (IOL), such as the shape, size and materials of the IOL implanted during cataract surgery has also been shown to affect the development of PCO. It has been shown that a sharp bend in the capsule, created by a capsule tension ring or an IOL with sharp optic edges, may induce contact inhibition of lens epithelial cell migration on the capsule.

Various anti-metabolites such as doxorubicin, methotrexate, mitomycin, daunomycin/daunorubicin, 5-fluorouracil and colchicine are effective in inhibiting lens epithelial cells proliferation in vitro. However, in vivo animal studies have shown that there are toxic side effects in the tissues of the eye when anti-metabolites are used in sufficiently high concentration to inhibit lens epithelial cells proliferation. In attempts to avoid side effects on other ocular tissues an immunotoxin specifically inhibiting proliferation of lens epithelial cells has been evaluated. The anti-lens epithelial cell monoclonal antibody binds specifically to lens epithelial cells and carries ricin or saporin that kill proliferating cells. In the experimental studies, antibodies against human antitransferrin and FGF have been used as antibodies against lens epithelial cells. However, no conclusive results have been obtained.

Another pharmacological approach is to separate lens epithelial cells from the lens capsule. Ethylenediamine tetraacetic acid (EDTA) was included in an irrigative solution and a simulated extracapsular cataract extraction was performed to separate lens epithelial cells. In other attempts, EDTA was used with a viscoelastic material (U.S. Pat. No. 5,204,331 to Nishi et al., 1993), or simply introduced into the lens capsule. When an EDTA solution was included in an irrigative solution and a simulated extracapsular cataract extraction was performed in cadaver eyes, the anterior lens epithelial cells could be separated. EDTA seems not to be more efficient than other agents evaluated in PCO prevention.

Enzymes such as trypsin and DISPOSE (protease) have also been evaluated for separation of lens epithelial cells. When a 2% trypsin solution was included in an irrigative solution and a simulated extracapsular cataract extraction was performed in cadaver eyes, lens epithelial cells were stripped in places. The cell separation was partially successful. However, the zonules were damaged by the trypsin solution. The use of an active enzyme can be a problem even when an enzyme solution is introduced into the lens capsule because it can damage the zonules bound to the lens capsule.

According to U.S. Pat. No. 4,909,784 to Dubroff 1990, when a cell-killing substance is introduced into the lens capsule through a small hole, without first removing the lens, lens epithelial cells are killed. A drawback when using this method is that the efficacy of the treatment may be strongly limited, if the natural lens is not removed before administrating the cell-killing substance. The natural lens may absorb or decrease the efficacy of the substance due to the huge number of lens epithelial cells within the lens. A viscoelastic material that is introduced into the anterior chamber prevents the active agent from escaping from the lens capsule, and prevents damage to the corneal endothelium. In related patents (U.S. Pat. No 4,909,784 to Dubroff 1990, U.S. Pat. No. 5,013,295 to Dubroff 1991), a syringe to remove the introduced substance from the lens capsule through a small hole was disclosed. However, physically and technically, it seems to be difficult to efficiently remove the substance introduced into the lens capsule before capsulorhexis without damaging the lens capsule. The remaining substance may escape from the lens capsule and damage the cells and tissues facing the anterior chamber during and after capsulorhexis.

SUMMARY OF THE INVENTION

In view of the drawbacks associated with prior art methods it is an object of the present invention to provide a method and compositions that allow safe elimination of proliferating lens epithelial cells during cataract surgery, thereby preventing the occurrence of PCO.

This object is achieved with a method according to claim 1.

The treatment/administration may be performed as an extra step in routine cataract surgery. It is quick and easy to learn and perform for all cataract surgeons.

From an economic point of view, development of a procedure to prevent PCO reduces the medical costs related to YAG laser capsulotomy, including the costs for the treatment, its complications, and YAG laser equipment.

As the active agent is administered locally on the inner surface of the lens capsule in a very efficient way, the required dose of the active agent is very low.

The method described in this patent application comprises the benefits of a removed lens during the local treatment of the lens capsule (compare with method according to U.S. Pat. No. 4,909,784 to Dubroff 1990, wherein the lens is not removed before treatment). Since the lens is never in contact with the active agents diminished absorption or activity of the agents is prevented. This assures that distribution over the whole capsule can be accomplished with an active agent solution of low concentration that will be minimally diluted or diffused into adjacent sensitive tissues.

The treatment/administration of the capsule may also be performed even if an IOL has been implanted, for example at initial indications of PCO development directly after or up to several years after the cataract surgery.

BRIEF DESCRIPTION OF THE DRAWINGS

The present invention will now become more fully understood from the detailed description given herein, wherein reference is made to the accompanying drawings, in which.

DETAILED DESCRIPTION OF THE PREFERRED EMBODIMENTS

First, a standard procedure for the removal of the lens 10 is illustrated with reference to FIGS. 1–2.

Figure 1:
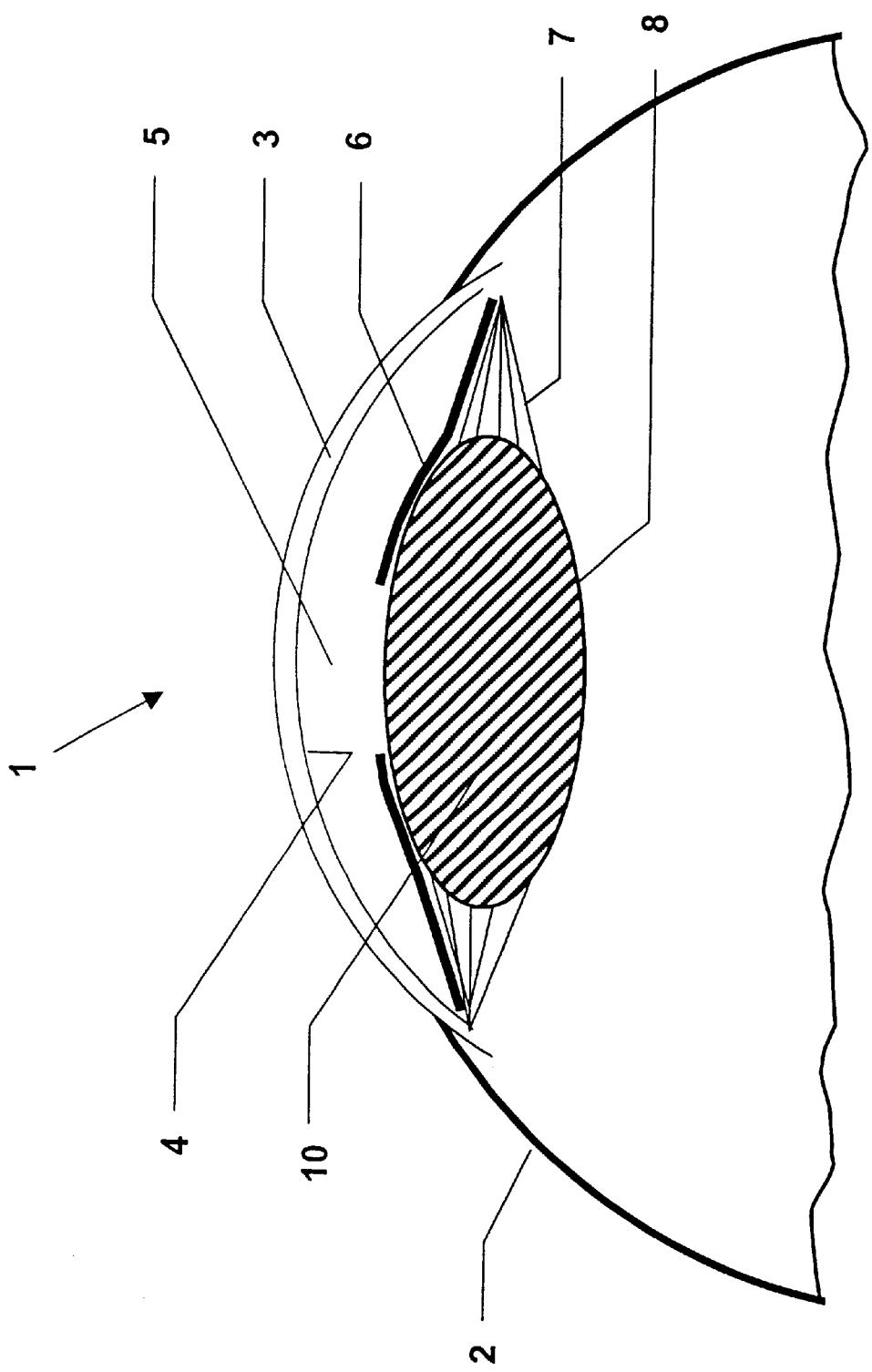
FIG. 1 shows a cross-sectional view of the human eye before surgery.
Figure 2:
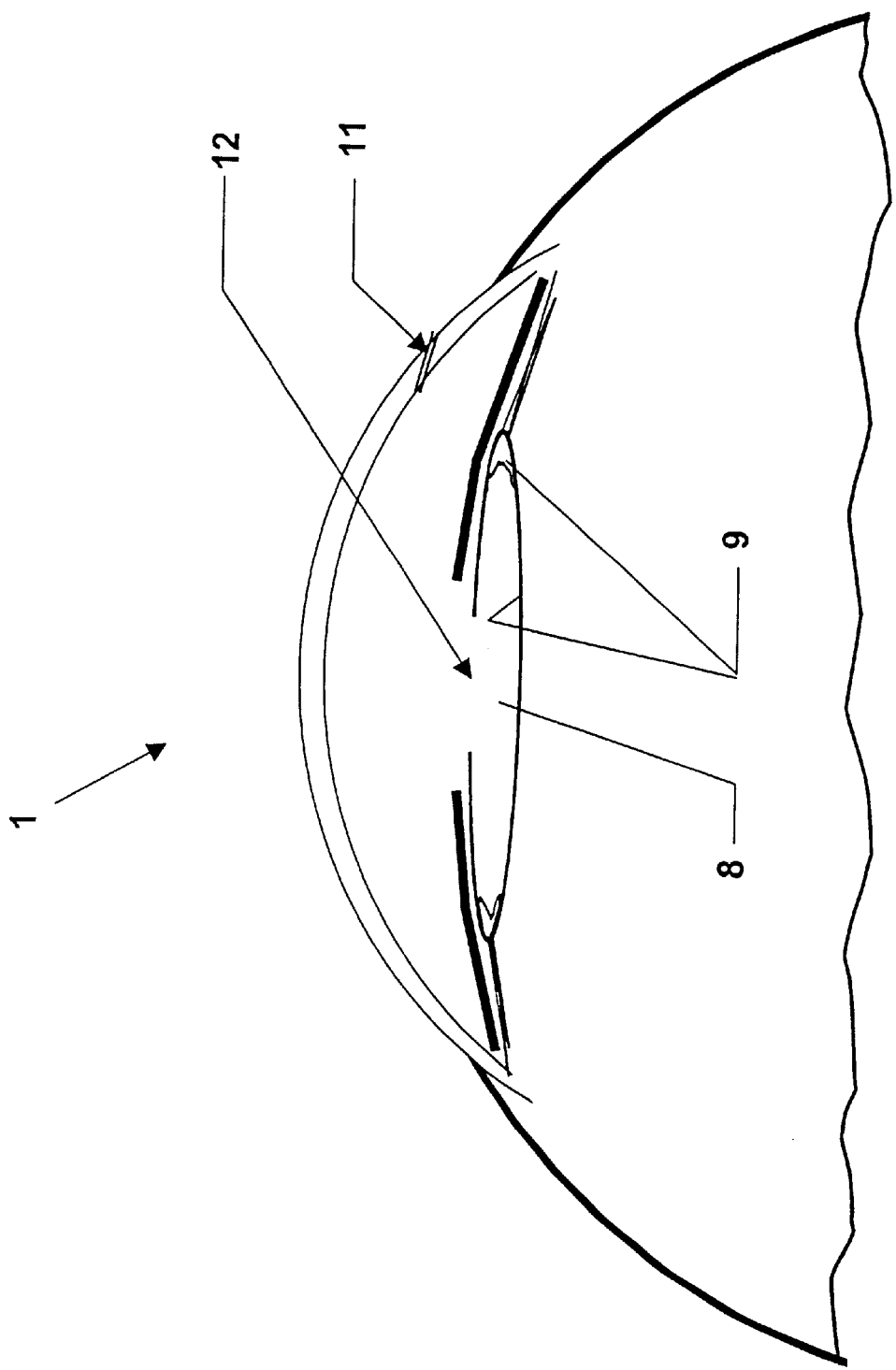
FIG. 2 shows a cross-sectional view of the human eye after lens extraction.
Figure 3:
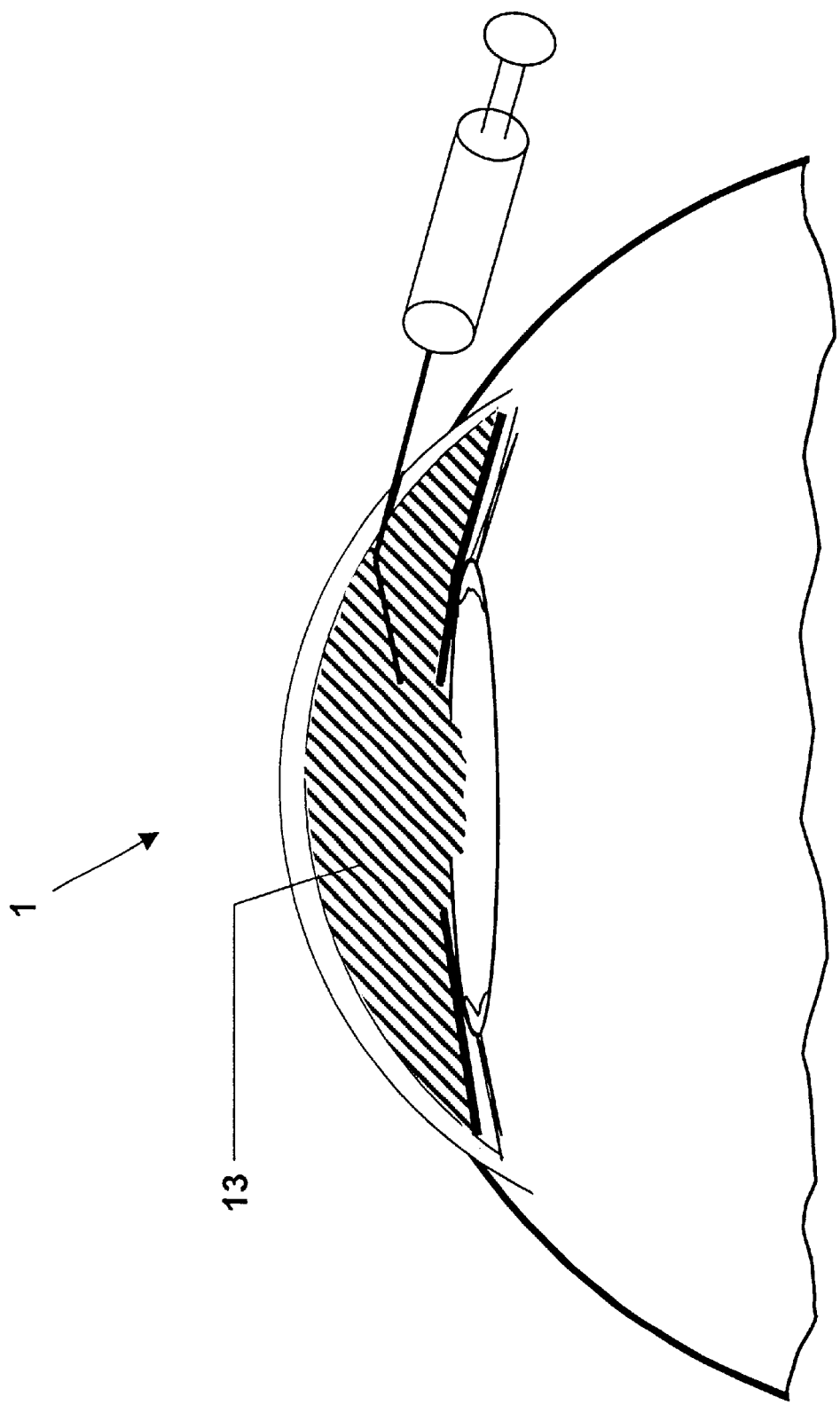
FIG. 3 shows a cross-sectional view of the human eye after injection of viscoelastic substance into the anterior chamber.

FIG. 1 schematically illustrates a human eye 1.

In the surgical extraction of the lens 10, an incision is made in the anterior part of the eye, in the cornea 3 or the sclera 2. Then a viscoelastic material 13 is introduced into the anterior chamber 5 to maintain the anterior chamber depth. An opening (capsulorhexis) 12 is made in the lens capsule 8.

Following capsulorhexis, the lens 10 is removed according to one of two principles: extracapsular cataract extraction (ECCE)—the cataractous lens 10 is squeezed out through an opening in the anterior lens capsule 8 and then removed through a 10–12 mm corneal incision 11, or phacoemulsification—the cataractous lens 10 is dissolved with a phaco-probe by high frequency sonification and rinsed out through a 3–4 mm corneal incision 11. Reference numbers 6 and 7 designate the iris and the zonular fibers, respectively, while reference number 4 designates corneal endothelial cells.

The method according to the present invention will now be illustrated with reference to FIGS. 3–7. When the lens 10 is removed, a viscoelastic solution 13 or equivalent solution is injected into the anterior chamber 5 (see FIG. 3)

The viscoelastic solution 13 should have certain rheological properties in order to confine the gas 14 within the lens capsule 8. A suitable substance is Healon5 (Pharmacia AB, Uppsala, Sweden) or similar viscoelastic solution. The viscoelastic solution 13 might be such that it has the ability to eliminate the toxicity of any active agent 15 escaping from the lens capsule.

Figure 4:
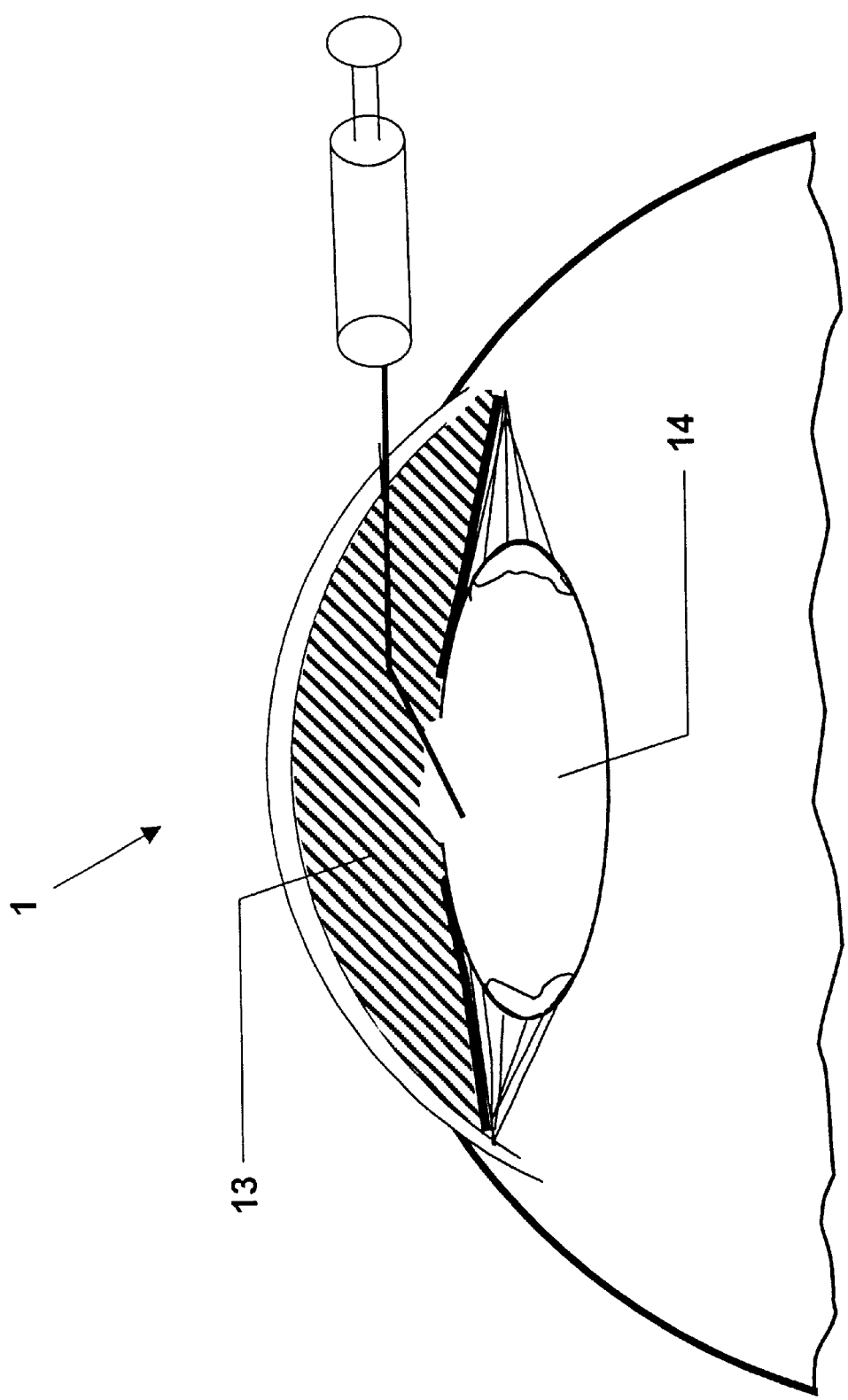
FIG. 4 shows a cross-sectional view of the human eye after injection of gas into the lens capsule.
Figure 5:
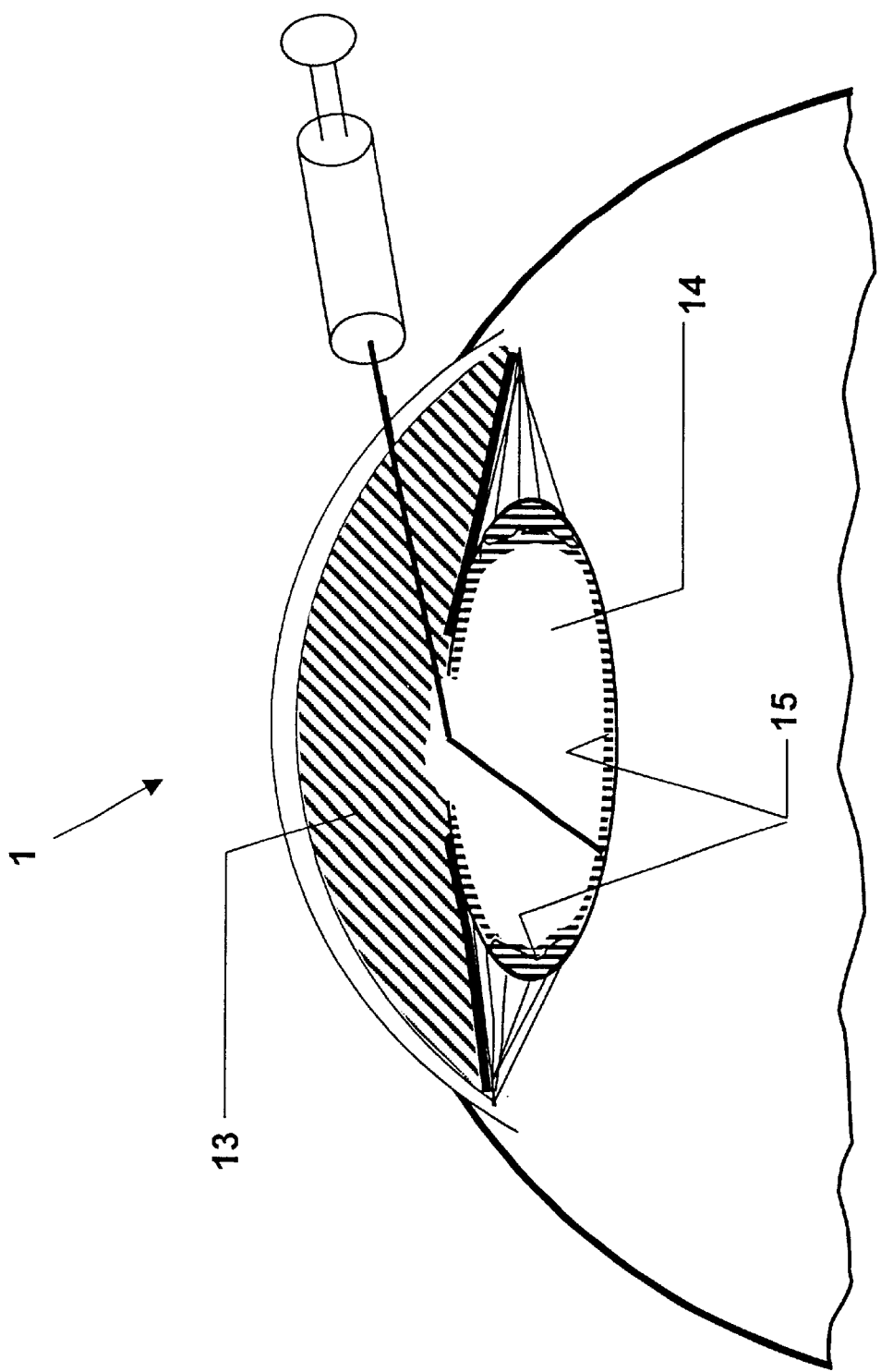
FIG. 5 shows a cross-sectional view of the human eye after application of an active agent within the lens capsule.

When the viscoelastic solution 13 is in position, a gas 14 is injected into the lens capsule 8, whereby the gas is confined by the pressure of the viscoelastic solution 13 (see FIG. 4). The gas is injected to keep the lens capsule 8 expanded during administration of an active agent.

Preferably, the gas 14 should not be reactive to tissues within the eye that is not aimed to be treated. The gas should not be reactive with water, i.e. create acidic or alkaline conditions. Instead, preferably it should be inert. The gas is preferable clear and/or invisible. It preferably comprises air, i.e., approximately 78% nitrogen and 21% oxygen.

The gas may be the active agent 15. The gas should then have the same effect on lens epithelial cells as the active agents described below.

Subsequent to the injection of the gas 14, an active agent solution 15 is injected onto the inner surface of the lens capsule 8. Due to the gas-expanded lens capsule 8, the administration of the active agent 15 becomes local and very efficient (see FIG. 5).

The active agent solution contains one or more agents with toxicity to lens epithelial cells 9. The inventive method prevents diffusion of the active agent to other parts of the eye. The concentration of the active agent should be such that it exerts the necessary effect but nothing more. Examples of possible active agents are doxorubicin, indomethacin, EDTA, 5-fluorouracil (5-FU), FGF-saporin, methotrexate, mitomycin, daunomycin/daunorubicin and colchicine, although any other active agent giving the desired effect is usable in the inventive method.

The active agent solution is preferably dyed to encourage safe and complete removal of the drug when finishing off the treatment. The dye should have equivalent or higher diffusion rate within viscoelastic solutions compared to the active agent. Then, the active agent does not reach to the corneal endothelial cells 4 before the dye does, which can be observed in the surgical microscope. Examples of dyes are trypan blue, fluorescein.

An alternative would be to use an active agent that is colored, e.g. trypan blue, or an active agent to which a dye has been bound, e.g. the dye fluorescein.

Diffusion of the active agent 15 from the lens capsule 8 to the surrounding viscoelastic solution 13 can easily be spotted because the active agent solution is colored. The dyed viscoelastic solution 13 can then be removed by for example an I/A-instrument 16. Diffusion of active agents to other parts of the eye can thus be prevented.

The administration of the active agent can also be followed by the addition of a second active agent, which have the ability to prevent or slow down further proliferation of lens epithelial cells 9 that might have survived the exposure to the first agent. The second active agent may be administered at the same time as the first one. It may also be so that only one active agent, having the properties of both the first and the second active agent, is administered.

The local treatment by the active agent 15 is performed for a specific time. Its duration has to be long enough to (irreversibly) damage or kill the lens epithelial cells 12. To prevent diffusion to other delicate tissues, this time should not be made longer than necessary.

Figure 6:
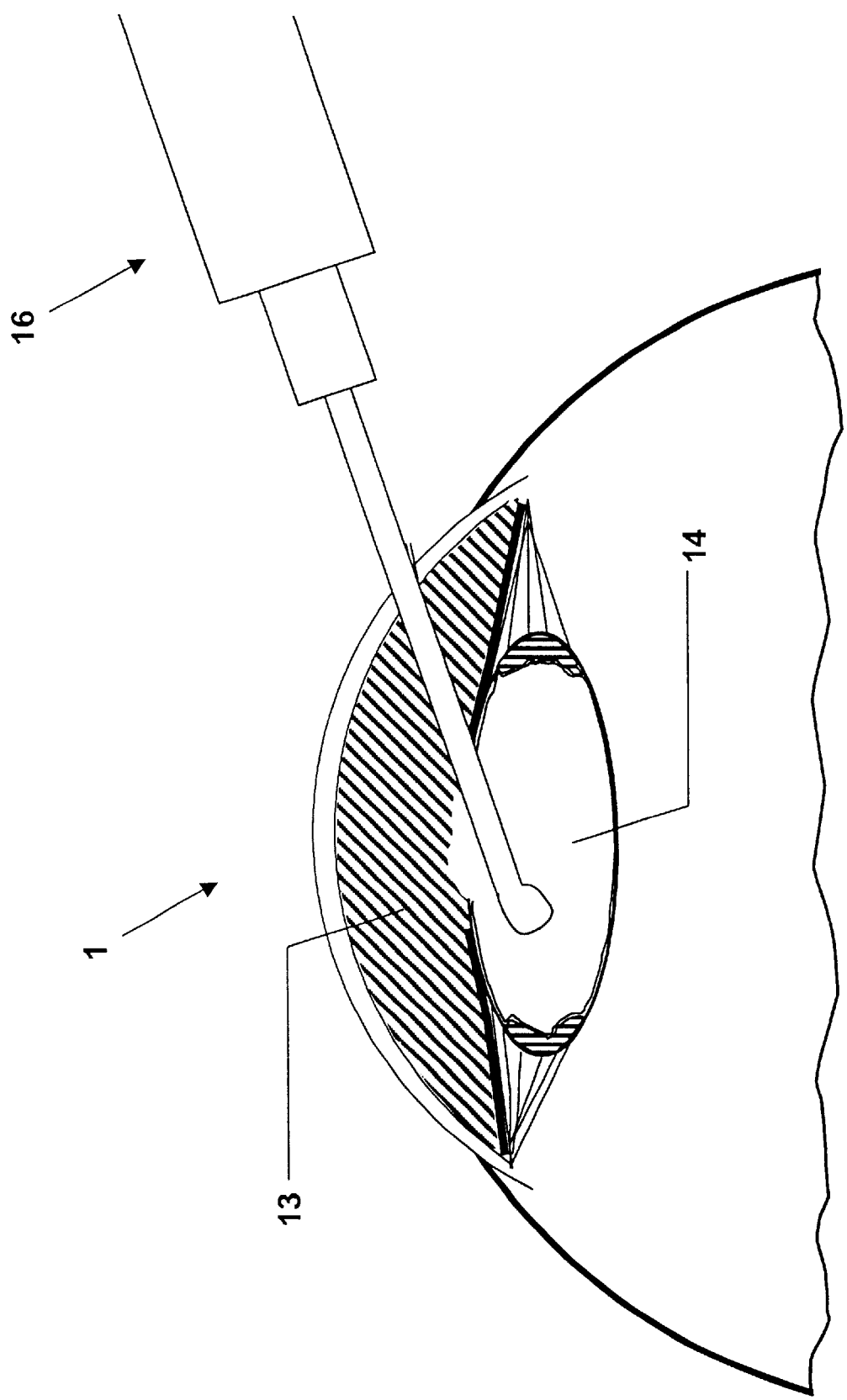
FIG. 6 shows a cross-sectional view of the human eye during irrigation and aspiration within the lens capsule.
Figure 7:
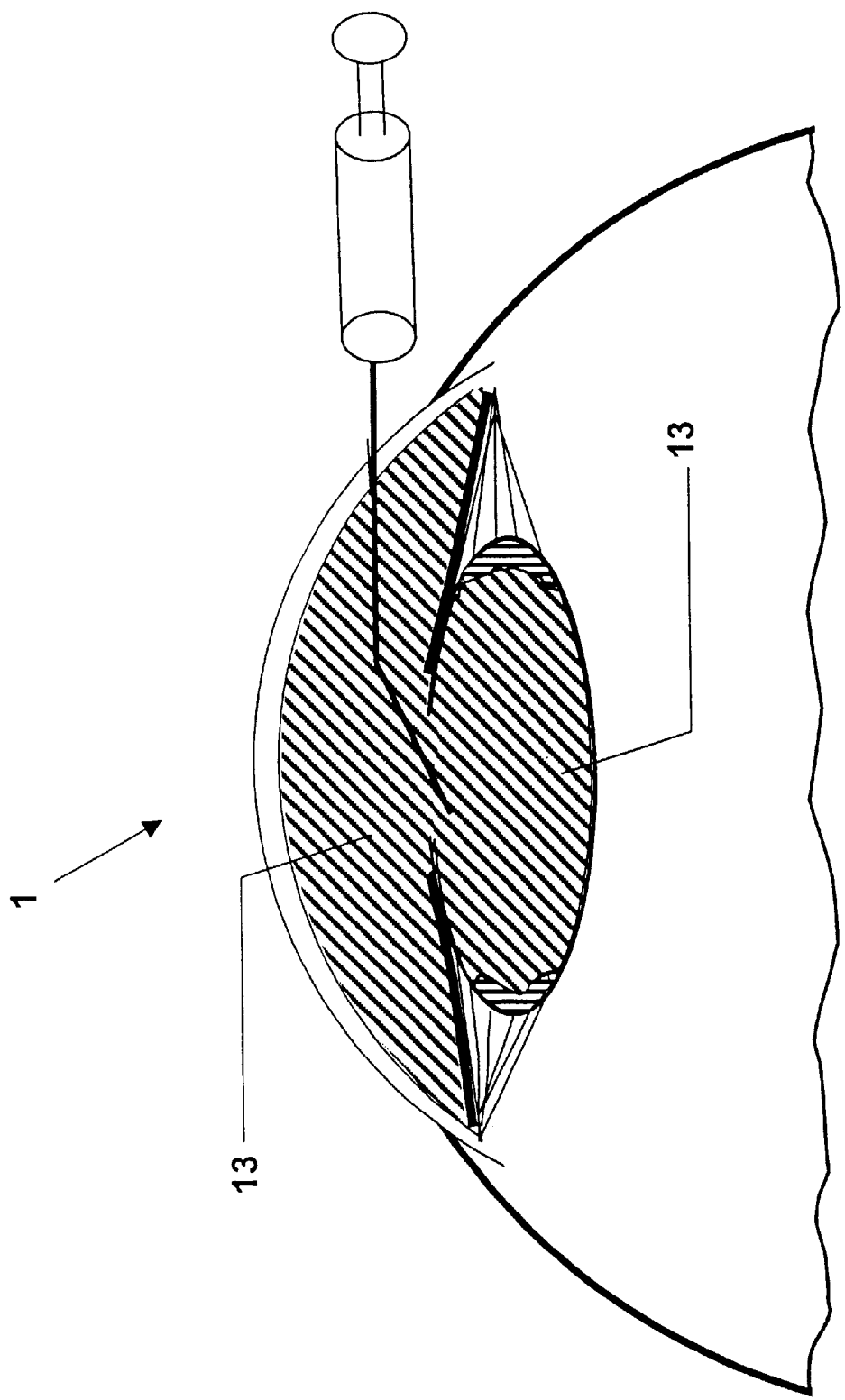
FIG. 7 shows a cross-sectional view of the human eye after injection of viscoelastic substance into the lens capsule.

The removal or inactivation of the active agent is performed by using an I/A-instrument 16 (see FIG. 6). It is a standard device used in surgical operations in the eye having an irrigative and aspirative ability. Mild settings have to be used with the I/A-instrument 16 to prevent the viscoelastic solution 13 within the anterior chamber 5 to be removed.

Before removal of the active agent by an I/A-instrument, the active agent may be inactivated by another agent, that may be administered in a similar way as the active agent, i.e. by application onto the inner surface of the air-filled capsule.

Injection of a viscoelastic solution 13 into the lens capsule 8 may be used to enhance implantation of an IOL or prevent contact between the treated area and other tissues. The viscoelastic solution may contain a substance that inactivates the toxic agent. The viscoelastic solution might be the same as being used in the anterior chamber 5.

The lens capsule 8 has to be intact and a proper capsulorhexis has to be created before using the described method. The method starts after complete removal of the cataractous lens 10 by using for example phacoemulsification. The treatment comprises the steps of:

a) filling anterior chamber 5 with a viscoelastic solution 13 (Healon5 or an similar solution with similar rheological properties),
b) injecting gas (e.g. air) 14 into the lens capsule 8, whereby the gas confined by the pressure of the viscoelastic solution 13, in order to maintain the depth of the anterior chamber 5 and to avoid dilution of the active agent solution 15,
c) injecting a colored solution of the active agent 15 within the air-filled area of the lens capsule 8, whereby the color indicates the distribution of the active agent 15, which helps to prevent displacement,
d) the active agent solution 15 is removed from the air-filled capsule 11 by irrigation and aspiration using an I/A-instrument 16, or inactivated by another agent administered into the capsule.

EXAMPLES

The method will now be described with reference to non-limiting examples of a method according to the present invention.

Example 1

Evaluation of a Preferred Embodiment of the Invention

Cataract surgery was simulated in porcine cadaver eyes. An eye was fixed on a plastic holder while maintaining a standardized intraocular pressure of 10–15 mm Hg before surgery. Further details of the model are published elsewhere (Holmen & Lundgren; submitted). The example was performed as follows:

1) A corneal incision 11 was performed at the limbus of the cornea 3;
2) The anterior chamber 5 was filled with a viscoelastic solution 13 (Healon5, Pharmacia AB, Uppsala, Sweden) by injection,
3) A continuous circular capsulorhexis was created;
4) Phacoemulsification was performed by an anterior segment operating system (Oertli Quinto, Oertli Instrumente AG, Berneck, Schweiz) with complete removal of the cataractous lens 10;
5) Additional viscoelastic solution 13 (Healon5) was injected into the anterior chamber 5;
6) The lens capsule 8 was filled with a gas 14 (78% nitrogen, 21% oxygen, 1% argon, i.e. fresh air) by injection;
7) An active agent solution 15 (fluorescein 10 µl/ml, no active agent) was applied onto the inner surface of the lens capsule 8, and distribution over the inner surface of capsule was noted;

8) A period of incubation, adjusted to be sufficient for dyeing the capsule 11, i.e. simulation of treatment of lens epithelial cells 9 by an active agent 15;

9) The active agent solution 15 was removed by irrigation and aspiration within the lens capsule 8 without removing the viscoelastic solution 13 in the anterior chamber 5;

10) Viscoelastic solution 13 in which the dye is diffused within is then removed in the same way; and 11) The lens capsule 8 is filled by a viscoelastic solution 13.

The efficiency of the inventive administration was evaluated visually in the surgical microscope, by slit lamp photography and by dissection. The photos and the dissected parts were examined visually with respect to distribution and leakage of the test solution.

During the phase of gentle injection of the colored test solution into the air-filled capsule 8 the solution was distributed all over its inner surface, as being observed in the surgical microscope.

No leakage of the colored substance through the capsulorhexis, i.e. into the anterior chamber, was observed.

Photos taken after application also showed that the capsule was colored and that there was no leakage. The same was found when dissecting the lens capsule.

In conclusion, the example indicates that the inventive method administers a small amount of solution efficiently, that is, the treating solution is selectively distributed on the aimed surface. The method also prevents diffusion of the active agent to other not targeted tissues.

Example 2

Example 2 was performed using the method described in Example 1, except for using trypan blue instead of fluorescein in the agent solution. The distribution of the active agent solution 15 was studied by free preparation of the lens capsule 8.

The results were equal to the ones in Example 1.

Example 3

Example 3 is performed using the method described in Example 1, but using a plurality of known active substances in the agent solution, e.g. doxorubicin, EDTA; indomethacin, 5-fluorouracil (5-FU), FGF-saporin, methotrexate, mitomycin, colchicine or daunomycin/ daunorubicin.

It should be understood that the detailed description and specific examples, while indicating preferred embodiments of the invention are given by way of example only. Various changes and modifications within the spirit and scope of the invention will become apparent to those skilled in the art from this detailed description.

What is claimed is:

1. A method of administration of substances active against lens epithelial cells, comprising the steps of:
    filling the anterior chamber (5) of an eye with a viscoelastic solution (13), to maintain the depth of the anterior chamber (5) and to prevent gas (14) from leaking out from the lens capsule (8),
    expanding the lens capsule (8) and keep it expanded, and injecting an active agent (14;15), toxic to lens epithelial cells, into the lens capsule (8).

2. The method according to claim 1, wherein the expansion of the lens capsule (8) is accomplished with a gas (14).

3. The method according to claim 2, wherein the gas (14) is the active agent.

4. The method according to claim 1, wherein said active agent (15) is injected in form of a solution onto the inner surface of the air-filled lens capsule (8).

5. The method according to claim 4, wherein the active agent (15) is a colored active agent.

6. The method according to claim 4, wherein the active agent (15) is an active agent to which a dye has been bound.

7. The method according to claim 4, wherein the active agent (15) is in a colored solution.

8. The method according to claim 1, wherein the active agent (15), after having (irreversibly) damaged or killed the lens epithelial cells (9), is inactivated in or removed from the lens capsule (8).

9. The method according to claim 1, comprising the step of coating the inner surface of the air-filled lens capsule (11) with a second active agent, capable of preventing cell growth and migration onto the posterior region of the capsule for as long as possible.

10. The method according to claim 9, wherein the addition of the second active agent is subsequent to the addition of the first active agent.

11. The method according to claim 9, wherein both the first and second active agents are administered at the same time.

12. The method according to claim 9, wherein an active agent having the properties of both the first and second active agents, is administered.

13. The method according to claim 1, wherein the viscoelastic solution (13) has the ability to eliminate the toxicity of the active agents.

14. The method according to claim 1, wherein the viscoelastic solution (13) has the ability to prevent diffusion of the active agents to adjacent tissues.

15. A method of preventing posterior capsule opacification (PCO) from occurring after cataract surgery, comprising the steps of:
    filling the anterior chamber (5) of an eye with a viscoelastic solution (13), to maintain the depth of the anterior chamber (5) and to allow confinement of gas (14) within the lens capsule (8), such that the gas (14) is prevented from leaking out from the lens capsule (8),
    expanding the lens capsule (8) by introducing the gas (14) and keeping said capsule expanded, and,
    injecting an active agent (14;15) on to the inner surface of the lens capsule (8), wherein said active agent is toxic to the lens epithelial cells, and whereby the administration of the active agent becomes local and efficient.

16. The method according to claim 1, wherein the gas (14) is the active agent.

17. The method according to claim 15, wherein said active agent (15) is injected in form of a solution onto the inner surface of the air-filled lens capsule (8).

18. The method according to claim 17, wherein the active agent (15) is a colored active agent.

19. The method according to claim 17, wherein the active agent (15) is an active agent to which a dye has been bound.

20. The method according to claim 17, wherein the active agent (15) is in a colored solution.

21. The method according to claim 15, wherein the active agent (15), after having (irreversibly) damaged or killed the lens epithelial cells (9), is inactivated in or removed from the lens capsule (8).

22. The method according to claim 15, comprising the step of coating the inner surface of the air-filled lens capsule

(11) with a second active agent, capable of preventing cell growth and migration onto the posterior region of the capsule for as long as possible.

23. The method according to claim 22, wherein the addition of the second active agent is subsequent to the addition of the first active agent.

24. The method according to claim 22, wherein both the first and second active agents are administered at the same time.

25. The method according to claim 22, wherein an active agent having the properties of both the first and second active agents, is administered.

26. The method according to claim 15, wherein the viscoelastic solution (13) has the ability to eliminate the toxicity of the active agents.

27. The method according to claim 15, wherein the viscoelastic solution (13) has the ability to prevent diffusion of the active agents to adjacent tissues.

28. The method of according to claim 15, comprising implanting an intraocular lens, filling the anterior chamber (5), expanding the lens capsule (8) and keep it expanded and injecting an active agent (14;15) into the lens capsule (8).

* * * * *